United States Patent [19]

Himmele et al.

[11] 4,105,669
[45] Aug. 8, 1978

[54] MANUFACTURE OF 2-AMINO-1-ALCOHOLS

[75] Inventors: Walter Himmele, Walldorf; Leopold Hupfer, Friedelsheim; Herbert Toussaint, Frankenthal; Gerhard Paul, Ludwigshafen, all of Fed. Rep. of Germany

[73] Assignee: BASF Aktiengesellschaft, Rheinland, Pfalz, Fed. Rep. of Germany

[21] Appl. No.: 807,925

[22] Filed: Jun. 20, 1977

Related U.S. Application Data

[62] Division of Ser. No. 730,828, Oct. 8, 1976.

[30] Foreign Application Priority Data

Oct. 24, 1975 [DE] Fed. Rep. of Germany ....... 2547654

[51] Int. Cl.$^2$ .................. C07D 263/14; C07C 85/145; C07C 85/20
[52] U.S. Cl. ............................. 260/307 F; 260/584 R
[58] Field of Search ..................................... 260/307 F

[56] References Cited

U.S. PATENT DOCUMENTS 4,014,880   3/1977   Dowd et al. ................. 260/307 F X

OTHER PUBLICATIONS

Frump, "Chemical Reviews", vol. 71, No. 5, pp. 483–505, (1971).

*Primary Examiner*—Winston A. Douglas
*Assistant Examiner*—John J. Doll
*Attorney, Agent, or Firm*—Keil, Thompson & Shurtleff

[57] ABSTRACT

Reaction of 1-hydroxy-2-ketones of the general formula R — CO — CH$_2$OH, where R is a short alkyl, with ammonia gives a new compound

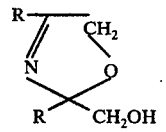

which on hydrogenation gives 2-amino-1-alcohols; the yield can be improved by carrying out the hydrogenation in the presence of ammonia.

2 Claims, No Drawings

MANUFACTURE OF 2-AMINO-1-ALCOHOLS

This is a division of application Ser. No. 730,828, filed Oct. 8, 1976.

U.S. Pat. No. 3,448,153 discloses that 1-hydroxy-2-ketones can be converted to the corresponding 2-amino-1-alcohols by batchwise reductive amination with ammonia and catalytically activated hydrogen. The process is carried out in the presence of a solvent, e.g. water, methanol or ethanol.

It has also been disclosed that reaction of ketones or aldehydes with ammonia or amines in the presence of hydrogen in reactors containing a fixed catalyst can also be carried out continuously, to give the corresponding substituted amines. Such processes are described, for example, in German Laid-Open Applications DOS 1,179,947 and 2,118,283.

It has not hitherto been possible economically to apply the continuous process to the conversion of 1-hydroxy-2-ketones. Using a fixed cobalt-containing unsupported or supported catalyst in a continuously operated tubular reactor, the yields of 2-amino-1-alcohol obtained are only from 15 to 50%, based on keto-alcohol employed. The remainder of the starting material is partially converted to the 1,2-diamino compound and partially to the 1,2-diol.

It is an object of the present invention to provide an economical process for the continuous conversion, in good yield, of 1-hydroxy-2-ketones to 2-amino-1-alcohols.

2-Amino-1-alcohols are used as emulsifiers and as intermediates for the synthesis of heterocyclic compounds, e.g. substituted piperazines and other pharmaceutical compositions. For example, 2-aminobutan-1-ol is used to produce ®"Ethambutol", a tuberculosis drug.

We have found that the above object is achieved and that aliphatic 1-hydroxy-2-ketones can be converted, in very good yield, to the corresponding 2-amino-1-alcohols by reacting a 1-hydroxy-2-ketone of the general formula R—CO—CH$_2$OH, where R is methyl, ethyl, n-propyl or n-butyl, at from about 0° and 120° C, with ammonia at from atmospheric pressure to about 300 bars, giving a compound of which the structure, according to examination by infra-red spectroscopy, nuclear magnetic resonance spectroscopy and mass spectroscopy, corresponds to an oxazoline of the formula (I)

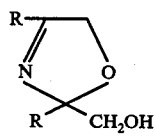

where R has the above meanings, and then treating this compound, by conventional methods, with hydrogen, in the presence or absence of ammonia, and in the presence of a hydrogenation catalyst.

The oxazolines of the formula (I) are new compounds.

Hitherto, only oxazolines of the general formula (II)

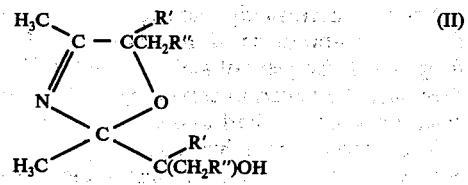

have been produced, starting from α-hydroxyketones which carry the OH group on a tertiary carbon atom (cf. J. Org. Chem. 28 (1963), 1,032).

The manufacture of the oxazolines (I) is carried out by reacting the hydroxyketone with ammonia at from about 0° to 120° C, preferably at from room temperature (20° C) to 80° C, at a pressure of from atmospheric pressure to about 300 bars, preferably up to about 100 bars. The reaction may be carried out without using extraneous solvents.

The compound (I) can be isolated in high yield by, for example, distillation. The yield of (I), based on 1-hydroxy-2-ketone employed, at atmospheric pressure is shown, for example, in the table which follows, as a function of the temperature.

| T (° C) | Yield (% I) R = C$_2$H$_5$ | R = CH$_3$ |
|---|---|---|
| 30 | 83 | 81 |
| 60 | 78 | 61 |
| 100 | 72 | 42 |

The compound need not be isolated before it is converted to the aminoalcohol.

In continuous operation, it is advantageous to introduce the hydroxyketone and at least a 5-fold molar excess of ammonia into a reaction tube which may be filled with any type of packing, e.g. glass Raschig rings, to effect better mixing of the reactants. The feed rate is, for example, from 60 to 100 g of hydroxyketone and from 80 to 300 g of ammonia per hour per liter of reactor volume. The reaction mixture of hydroxyketone and ammonia can be fed directly to a high pressure tube, filled with a fixed catalyst, which tube acts as the reactor for the subsequent hydrogenating amination.

The hydrogenating amination is carried out at from 90° to 130° C, preferably from 100° to 120° C, and at from 100 to 300 bars, preferably from 120 to 250 bars. Suitable hydrogenation catalysts are conventional unsupported or supported catalysts, preferably containing cobalt, which are modified with elements or compounds of elements of main group 5, preferably phosphorus, with or without elements of subgroup 1, preferably copper, and of subgroups 6 to 8 of the Periodic Table, preferably chromium, manganese and/or nickel. In general, these are conventional catalysts and are treated with hydrogen at from 200° to 280° C prior to the reaction. After this treatment, the catalyst constituents, except for the carrier, are believed to be present in the elementary form. The manufacture and use of suitable catalysts has been disclosed and is described, for example, in German Published Application No. 1,259,899. The hydrogenating amination can be carried out without using extraneous solvents.

In order to obtain a good yield of aminoalcohol from the hydrogenating amination of the oxazoline it is generally necessary to provide at least a three-fold molar amount of ammonia, based on the original hydroxyketone. If smaller amounts of ammonia are used, the dialkyl piperazines corresponding to the desired aminoalcohol are increasingly obtained, in various isomeric forms, as by-products. If the oxazoline (I) is solely hydrogenated, the yield of aminoalcohol is, logically, less then 50%; however, in certain cases this may be desirable, if it is also desired to obtain other by-products.

The reactor for the hydrogenating amination is suitably fed, in the process according to the invention, with from 0.02 to 0.3 kg of reaction mixture, comprising hydroxyketone and ammonia, per hour per liter of reactor volume, preferably with from 0.05 to 0.2 kg per liter per hour, with or without additional ammonia. The product obtained at the reactor outlet contains only a small amount of high-boiling constituents and (leaving out of account the excess ammonia and the water formed in the reaction) generally about 75 to 95% of the desired 2-amino-1-alcohol. The yield is, for example, from 86 to 93% for a conversion of from 80% to 100%. The pure 2-amino-1-alcohol can be isolated from the reaction mixture by conventional processes, preferably by rectification.

EXAMPLE 1 a. Batchwise pre-reaction under atmospheric pressure.

3 kg of 1-hydroxybutan-2-one are placed in a 4 liter glass flask and gaseous ammonia is passed in at room temperature and atmospheric pressure, whilst stirring, until no more ammonia is absorbed. At that stage the weight increase is 500 g. Subsequent titration with HCl shows that the solution still contains 4.5 mmole/g of free ammonia. A carbonyl band is no longer visible in the IR-spectrum. It is possible to isolate, by distillation, a yield of 2,240 g of a single compound (boiling point 72° – 74° C/0.3 mm Hg) which, according to the elementary analysis and NMR spectrum, is pure and corresponds to formula (I) given above.

b. Continuous pre-reaction under superatmospheric pressure.

A high pressure tube filled with 0.5 liter of glass Raschig rings is fed continuously with 30 g/hour of 1-hydroxybutan-2-one and 40 g/hour of ammonia at 40° C and 200 bars. The reaction mixture taken off is directly subjected to the hydrogenating amination. A sample taken off at the end of the reactor shows that the conversion of the 1-hydroxybutan-2-one is complete.

c. Reductive amination.

A tubular catalyst-filled 5 liter high pressure reactor is used. The catalyst consists of 4 mm thick extrudate containing 90.5% of cobalt oxide, calculated as CoO, 5.5% of manganese oxide calculated as MnO, and 4.0% of phosphoric acid. First, the catalyst is activated by passing over it a mixture of hydrogen and nitrogen, at 300° C for 12 hours. The reactor is then fed continuously, at 110° C under a hydrogen pressure of 200 bars, with 1,000 ml/hour of the above reaction mixture and, in addition, 15,000 ml/hour of liquid ammonia. 50 liters (S.T.P.) of off-gas are taken from the reactor per hour. The reaction product contains 1.7% of high-boiling constituents not identified by gas chromatography and, according to analysis by gas chromatography (leaving the excess ammonia and the water formed in the reaction out of account), 90.3% of 2-aminobutan-1-ol, 1.0% of diethylpiperazines, 0.8% of 1,2-diaminobutane, 0.9% of 1,2-butanediol and 4.7% of a compound which, according to analytical determination, corresponds to the above formula (I), i.e. has presumably not been converted.

EXAMPLE 2

The reductive amination is carried out as in Example 1c, but the hydrogenation reactor is fed with 1,000 ml/hour of the reaction mixture of Example 1b, without additional ammonia. According to analysis by gas chromatography, the reaction product contains 93.7% of 2-aminobutan-1-ol, 1.6% of diethylpiperazines, 1.0% of 1,2-diaminobutane, 0.8% of 1,2-butanediol, 0.8% of the compound according to formula (I) and 4.8% of high-boiling constituents not detected in the gas chromatogram.

EXAMPLE 3

The reductive amination is carried out as in Example 1c, but the reactor is fed with 600 ml/hour of the reaction mixture of Example 1a, without additional ammonia. According to gas chromatography, the product contains 77.8% of 2-aminobutan-1-ol, 10.5% of diethylpiperazines, 1.0% of 1,2-diaminobutane, 6.8% of 1,2-butanediol and 1.2% of a compound of the formula (I), in addition to 15% of a residue not identified by gas chromatography.

EXAMPLE 4

The procedure of Example 1c is followed, but the reactor is charged with a catalyst which contains 70.6% of cobalt oxide, calculated as CoO, 4.3% of manganese oxide, calculated as MnO, 2.0% of molybdenum, calculated as MoO, 20.0% of copper oxide, calculated as CuO, and 3.1% of phosphoric acid, and which has been converted to 4 mm extrudates. According to analysis by gas chromatography, the product consists of 84.3% of 2-aminobutan-1-ol, 2.8% of diethylpiperazines, 4.2% of 1,2-diaminobutane, 1.0% of 1,2-butanediol and 3.0% of compound (I), in addition to 3.9% of a high-boiling constituent not identified by gas chromatography.

EXAMPLE 5

The procedure of Example 3 is followed, but the reactor is charged with a catalyst which contains 8% of CoO, 8% of NiO and 3% of CuO on an aluminum oxide carrier and is in the form of 4 mm extrudates. According to analysis by gas chromatography, the product consists of 73.4% of 2-aminobutan-1-ol, 1.4% of diethylpiperazines, 1.1% of 1,2-diaminobutane, 1.2% of 1,2-butanediol and 20.8% of the compound corresponding to the formula (I). The high-boiling constituent not identified by gas chromatography amounts to 5.5%.

EXAMPLE 6

The procedure of Example 2 is followed but instead of 1-hydroxybutan-2-one, hydroxyacetone is used. The reaction mixture is subjected to hydrogenating amination exactly as described in Example 3. The product leaving the reactor contains 5.1% of a high-boiling constituent not identified by gas chromatography, 81.3% of 2-aminopropan-1-ol, 1.6% of dimethylpiperazines, 1.5% of 1,2-propanediol and 12.2% of a compound of the formula (I).

EXAMPLE 7

The procedure of Example 3 is followed but the reactor is fed with 400 ml/hour of 1-hydroxybutan-2-one and 4,000 ml/hour of liquid ammonia. According to gas chromatography, the product leaving the reactor contains 37.8% of 2-aminobutan-1-ol, 48.0% of 1,2-butanediol and 11.3% of 1,2-diaminobutane.

We claim:
1. A compound of the formula
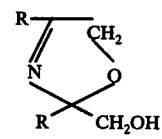
where R is methyl, ethyl, n-propyl or n-butyl.
2. A compound as set forth in claim 1, wherein R is methyl.
* * * * *